United States Patent [19]

Macel

[11] Patent Number: 6,048,981
[45] Date of Patent: Apr. 11, 2000

[54] MAGNESIUM OMEPRAZOLE AND PROCESS FOR ITS PREPARATION

[75] Inventor: Bob Macel, Thornhill, Canada

[73] Assignee: Torcan Chemical Ltd., Aurora, Canada

[21] Appl. No.: 09/064,161

[22] Filed: Apr. 22, 1998

[51] Int. Cl.[7] ................................................. C07D 401/00
[52] U.S. Cl. ........................................................ 546/273.4
[58] Field of Search .......................................... 546/273.4

[56] References Cited

FOREIGN PATENT DOCUMENTS 1264751   1/1990   Canada .
2166794   3/1997   Canada .
WO 97/41114  11/1997   Sweden .

*Primary Examiner*—Dwayne C. Jones
*Attorney, Agent, or Firm*—Ridout & Maybee

[57] ABSTRACT

Magnesium omeprazole is provided, in a form free of organic solvent residues and free of traces of more than 50 ppm of another metal ion. It is prepared by an aqueous phase process in which a solution of omeprazole in concentrated aqueous ammonia is added to a mixture of a magnesium salt and a fully ionized ammonium salt, in aqueous solution, to effect precipitation of magnesium omeprazole.

8 Claims, No Drawings

MAGNESIUM OMEPRAZOLE AND PROCESS FOR ITS PREPARATION

FIELD OF THE INVENTION

This invention relates in general to water insoluble salts of benzimidazoles, and more particularly to the magnesium salt forms of the drug substance called omeprazole, and processes for its preparation.

BACKGROUND OF THE INVENTION

Omeprazole is a well known pharmaceutical useful for inhibiting gastric acid secretion and for providing gastrointestinal cytoprotection effects in man. It may be used for prevention and treatment of gastrointestinal inflammatory disorders, including gastritis, gastric ulcer and duodenal ulcer. Chemically omeprazole is 5-methoxy-2-[[(4-methoxy-3,5-dimethyl-2-pyridinyl)methyl]sulfinyl]-1H-benzimidazole, of formula I:

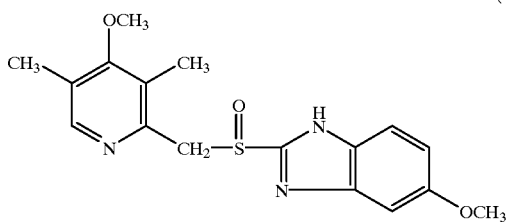

Various basic salts of omeprazole, such as omeprazole magnesium and omeprazole sodium, are known and described in the patent and scientific literature. Magnesium omeprazole is an example of what are called basic salts or basic addition salts of omeprazole, these terms being used herein synonymously. Magnesium omeprazole, as the term is used herein, means salts formed between one magnesium di-cation and two omeprazole anions. These salts may contain water of hydration, residual organic solvents, traces of free base omeprazole and traces of inorganic salt impurities.

A problem with omeprazole is its stability characteristics. Upon storage without any precautions being taken, it is reported to be degraded at an undesirably high rate. During storage under accelerated stability conditions, e.g. at 37° C. and a relative humidity of 80% for a period of six months, about 6% of the substance is converted to degradation products. Although decomposition under normal storage conditions is lower, it is desirable to obtain omeprazole derivatives which exhibit improved stability.

BRIEF REFERENCE OF THE PRIOR ART

Canadian Patent 1,264,751 Brandstrom describes the lithium, sodium, potassium, magnesium, calcium, titanium, quaternary alkyl ammonium and guanidinium salts of omeprazole. Two methods of forming omeprazole basic salts are exemplified. In one indirect method sodium omeprazole is first formed from omeprazole and 50% sodium hydroxide in tetrahydrofuran, and the salt is then caused to crystallize by mixing in trichloroethylene. Magnesium omeprazole is then prepared by mixing this omeprazole sodium dissolved in de-ionized water with magnesium chloride dissolved in de-ionized water. This method has the disadvantages (i) that the method is indirect; (ii) that organic solvents are used in the formation of the sodium omeprazole, including the environmentally troublesome trichloroethylene, and (iii) that the product must be washed exhaustively with water to eliminate sodium chloride. A second procedure is given in Example 6 of this Canadian Patent. Magnesium is reacted with absolute methanol to give magnesium methoxide in methanol, which is added to omeprazole dissolved in methanol. The omeprazole magnesium is recovered by evaporation of the solvent. This procedure cannot be practiced on a large scale because of the need to evaporate to dryness. It has been found that unacceptable and potentially dangerous amounts of methanol become trapped in this solid, making it pharmaceutically unacceptable.

Canadian Patent Application 2,166,794 Källström et al., derived from WO95/019707, describes a magnesium omeprazole preparation, claimed to be advantageous for producing a pharmaceutical formulation. The process by which the magnesium omeprazole is prepared is a variant of Example 6 of aforementioned Canadian Patent 1,264,751. The omeprazole magnesium is prepared from magnesium alkoxide in alkanol (preferably methoxide in methanol) and omeprazole. Then instead of evaporating the solvent, the solution is concentrated and either centrifuged or filtered to remove inorganic contaminants. Finally, de-ionized water is gradually added to the alkanol solution causing the omeprazole salt to crystallize. The magnesium omeprazole produced by this process is claimed to have particularly advantageous properties.

This process for preparing magnesium omeprazole suffers from a number of significant disadvantages. The product is very difficult to prepare reproducibly and substantially free of alkanol solvent. The process is most preferably conducted in practice with magnesium methoxide, and methanol is toxic. It has been found that the magnesium omeprazole is in a metastable condition when dissolved in methanol alone, and it can and does precipitate out. Thereafter, it is in a form which cannot be re-dissolved by even doubling or tripling the amount of solvent, with or without heat, unless the solid is isolated and dried first in vacuum before attempting the dissolution.

It is desirable for preparing magnesium omeprazole to have a process which avoids the use of organic solvents by being operated in water, which prepares the magnesium omeprazole substantially free from organic salts, and which gives a product free of metal species other than magnesium.

Any process for making magnesium omeprazole in aqueous media must address the problem that magnesium hydroxide will have a significant tendency to co-precipitate, because the solubility product of magnesium hydroxide is only $1.5 \times 10^{-11}$.

SUMMARY OF THE INVENTION

It is an object of the present invention to provide a process for preparing magnesium omeprazole which results in a product which is essentially or entirely free of organic solvent residues, i.e. the level of organic solvent residues is no greater than would be expected if the only source of organic solvent were the pharmaceutically pure omeprazole itself.

It is a further object to provide a process which produces magnesium omeprazole which is essentially free of inorganic salt contaminants.

It is a further object to provide such a process which yields the magnesium omeprazole in a form essentially free of other metal ions besides magnesium.

It is a further object to provide a process which produces magnesium omeprazole with a degree of crystallinity useful and advantageous for pharmaceutical formulation on an industrial scale.

The present invention provides an aqueous phase process for preparing magnesium omeprazole in which a homogeneous solution of omeprazole in concentrated aqueous ammonia is mixed with a magnesium salt and an effective amount of a fully ionized ammonium salt, in aqueous solution, the ammonium ion concentration being at least equal to the magnesium ion concentration on a molar basis. From this mixture, magnesium omeprazole crystallizes in a desirable crystalline form, without at the same time causing precipitation of magnesium hydroxide. The magnesium omeprazole so obtained is essentially free of other metal cations besides magnesium, since the only other sources of metal ions other than magnesium are the water used, the concentrated ammonia solution used, the magnesium salt starting material and the pharmaceutically pure omeprazole.

Whilst it is not intended that the scope and operation of this invention should be in any way limited by theory or by its mode of operation and possible explanations thereof, it is believed that the ammonium ion present in the solution suppresses the concentration of hydroxide ion so that the solubility product of magnesium hydroxide is not exceeded. At the same time and synergistically, the ammonia dissolves and holds the omeprazole ready to react without producing unacceptable levels of hydroxide ion in the presence of magnesium ion.

The process of the present invention is extremely simple. It is the direct combination of a magnesium salt with a base and omeprazole, in water. It is contraindicated in that it is known that magnesium salts in aqueous basic solution precipitate magnesium hydroxide. That this does not happen at any time throughout the procedure of mixing together the ammoniacal solution of omeprazole and the solution of magnesium salt/ionized ammonium salt is surprising. It depends on the unknown solubility product of magnesium omeprazole in ammonia/ammonium salt solution and the kinetic rate of crystallization of magnesium omeprazole from this solution. Simple as it is in practice, it is nonetheless advantageous.

In any event, the process of the present invention provides magnesium omeprazole having a degree of crystallinity equal to that produced by the prior art disclosures disclosed in Canadian Patent Application 2,166,794, and without exposure to organic solvents and without resulting in any organic solvent residues trapped in the crystal lattice.

DESCRIPTION OF THE PREFERRED EMBODIMENTS

The chemical process of the present invention, in one embodiment, may be depicted as follows:

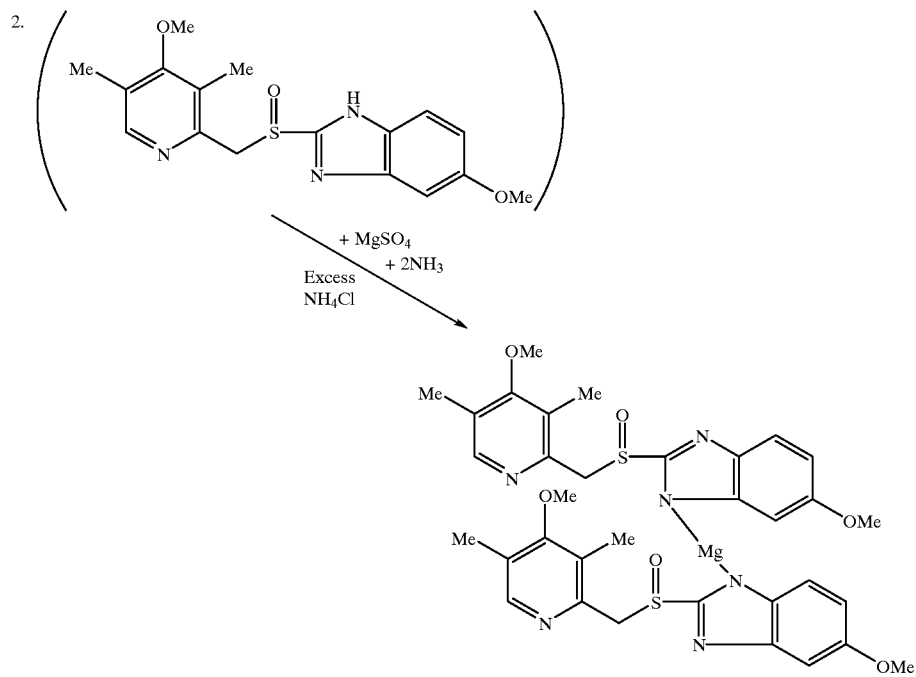

This choice of specific magnesium and ammonium salts in the above process is optional and generally preferred, but not essential, as described below.

Since some essentially ionized ammonium salts are reported to be sublimeable under vacuum, the practice of the process of this invention using such salts and using the magnesium salt of the same anions, followed by drying under an effectively high vacuum and effective temperature which is at the same time less than the decomposition temperature of magnesium omeprazole, produces magnesium omeprazole entirely free of ions other than magnesium and omeprazole anion. This constitutes a preferred embodiment of the invention.

Ammonium salts useful in the present invention are pharmaceutically acceptable fully ionized ammonium salts of strong inorganic or organic acids which are readily soluble in water. These include ammonium sulfate, ammonium chloride, ammonium nitrate, ammonium bromide and their stoichiometric hydrates.

The magnesium salts used in the present process are pharmaceutically acceptable, water soluble, appreciably ionized salts. Examples include magnesium halides (especially magnesium chloride), magnesium sulfate, magnesium nitrate and the like, with magnesium sulfate and magnesium chloride being especially preferred. Particularly useful are inexpensive salts which form stable stoichiometric hydrates, because these are reproducibly pure and dissolve readily in water. The number of moles of the ammonium salts per mole of magnesium is preferably greater than 3, and preferably greater than 5. The use of the stoichiometric and nonstoichiometric hydrates, ammonia solvates and mixed magnesium ammonium salts is also within the scope of the invention. Also useful, but less preferred, are other magnesium salts such as magnesium perchlorate and other non-pharmaceutical salts, some of which have special practical advantages such as price, purity, etc. The stoichiometry between the omeprazole and the magnesium salts should be between 1.95 and 2.05, most preferably between 1.99 and 2.01. The practitioner will appreciate that in general the closer the ratio of the moles of magnesium reagent to the moles of omeprazole material is to the stoichiometrically correct 1:2, generally the easier it will be to obtain highly pure final product. Routine trials to reach optimal balance of yield and purity can be conducted prior to final scale-up to an industrial process.

The particle size of magnesium omeprazole can be controlled as desired, by mechanical grinding and/or sieving, as well as by adjustment, in the preparation itself, of the parameters well-known to control particle size.

Concentrated aqueous ammonia (ammonium hydroxide) is, of course, distinctly basic. If a solution of concentrated aqueous ammonia is mixed with a solution of the magnesium salt of a strong acid, such as magnesium chloride or magnesium sulfate, one can expect an immediate precipitation of gelatinous magnesium hydroxide, since its solubility product $[Mg^{2+}][^-OH]^2$ will be exceeded. However, the concentration of hydroxyl ion in an aqueous ammonia solution is determined by the extent of the reaction of ammonia with water:

$$NH_3 + H_2O \rightleftharpoons [NH_4^+] + [OH^-]$$

The equilibrium constant for the reaction, $K_b$, is:

$$K_b = \frac{[NH_4^+][OH^-]}{[NH_3]} = 1.80 \times 10^{-5}$$

Since the number of ammonium cations is exactly the same as the number of hydroxyl anions, this equation can be simplified to $$K_b = \frac{[OH^-]^2}{[NH_3]} \quad \text{or} \quad [OH^-] = (K_b[NH_3])^{1/2}$$

and it is seen that the concentration of hydroxyl ion in the solution is proportional to the square root of the ammonia concentration.

When a fully ionized ammonium salt $NH_4X$, for example ammonium chloride or ammonium sulfate, is introduced, the situation changes, the concentration of ammonium ions $[NH_4^+]$ being effectively equal to the concentration of the added salt, i.e. $[NH_4X]$, so that $$K_b = \frac{[NH_4X][OH^-]}{[NH_3]} \quad \text{or} \quad [OH^-] = \frac{K_b[NH_3]}{[NH_4X]}$$

Accordingly, the concentration of hydroxide can be reduced by adding ionized ammonium salts, $NH_4X$, because as the concentration of ammonium salt $[NH_4X]$ increases, the hydroxyl concentration $[^-OH]$ decreases—the "common ion" effect.

In the process of the invention, it is preferred to pre-form a solution of omeprazole in concentrated ammonia, and to add this to a pre-formed aqueous solution of magnesium salt (preferably magnesium chloride) and ammonium salt (preferably ammonium chloride), so that the magnesium ion is in excess during the mixing procedure. However, other orders of addition can be used if the process is conducted carefully, such as mixing the omeprazole, ammonia and ammonium salt first, and adding the magnesium salt to this mixture, or, less desirably, pre-mixing the magnesium salt and ammonium salt, and adding this mixture to pre-formed omeprazole/ammonia solution.

In the process of the present invention, $[OH^-]$ is arranged to be so low, by this method, that magnesium hydroxide does not precipitate from the aqueous solution. Omeprazole dissolved in concentrated aqueous ammonia is added into an aqueous mixture of a magnesium salt such as magnesium sulfate, ammonium salt such as ammonium chloride and water. The magnesium omeprazole precipitates, and can be simply filtered and washed to free it from ammonia and ammonium salts. It can be dried to give a solid which is completely free of organic solvent residues.

SPECIFIC DESCRIPTION OF THE MOST PREFERRED EMBODIMENTS

The process of the present invention is further described in the following non-limiting, illustrative specific example.

EXAMPLE

Into a 500 ml three-necked round bottom flask equipped with a mechanical stirrer, thermometer and inert gas source, was introduced 50.0 g of de-ionized water. The water was heated in the flask to 45–50° C., and 3.48 g of anhydrous magnesium sulfate was added gradually as a stream of powder to the heated water, under vigorous stirring. A clear solution was formed. The solution was cooled to 30–35° C., and 8.00 g of ammonium chloride was added, all at once. The mixture was stirred to effect complete dissolution, and cooled to 24–26° C. A clear translucent white magnesium salt-ammonium salt aqueous solution formed.

Into a 500 ml single-necked round bottom flask equipped with a magnetic stirrer and a nitrogen-bubbler was introduced 20.00 g of omeprazole. The bubbler was removed, and 200 ml of 26–32% aqueous ammonia run into the flask. The slurry was stirred under nitrogen until the solids dissolved. The solution, of volume 220 ml and at a temperature of 20–25° C., was transferred to a dropping funnel.

Whilst maintaining the temperature at 20–26° C., the omeprazole solution was introduced into the magnesium salt-ammonium salt aqueous solution prepared above, under vigorous stirring. A white precipitate formed immediately. The flask in which the omeprazole solution had been formed and the dropping funnel in which it had been stored were rinsed with 5.0 ml of 26–32% aqueous ammonia, and the rinsings added to the reaction mixture, to obtain as complete a transfer of the omeprazole as reasonably possible. The reaction mixture was stirred at 20–26° C. for 20–30 minutes, and filtered on a Buchner filter using a filter paper wetted with de-ionized water. The filter flask was washed into the filter cake with 2 aliquots of 20 ml de-ionized water. The wet filter cake was removed from the Buchner and placed in a 500 ml beaker equipped with a magnetic stirrer. The filter paper was carefully removed. An aqueous slurry was formed in the beaker by addition of 200.0 ml of de-ionized water, and 10.0 ml of 26–32% aqueous ammonia was added to the slurry, to provide a more rapid filtration. After gently stirring the slurry for 20 minutes at 20–25° C., to break it up into finer solid, it was filtered on the same Buchner filter, washed with 3 aliquots of 50 ml de-ionized water, with trituration for 5 minutes for each aliquot, thereby removing residual ammonium chloride and ammonium sulfate by-product. Then the solid was dried under vacuum at 40–45° C. to constant weight (16 hours), to yield a white-light yellow powder in near quantitative yield. This product was identified by its IR spectrum. By inductively coupled plasma analysis, it was determined to contain 3.2–3.6% magnesium. It had a moisture content of about 8–10% and undetectable heavy metals (<0.0004%) Sodium determination by ICP was<50 ppm. The purity by HPLC was greater than 99.9% and by titration between 97 and 103% estimated on a dry basis there were no detectable organic solvent residues and the degree of crystallinity was equal to that of material prepared according to Canadian patent application 2,166, 794.

What is claimed is:

1. An aqueous phase process for preparing magnesium omeprazole, which comprises preparing, in an aqueous medium essentially free of organic solvent, a mixture of a magnesium salt, omeprazole, a fully ionized ammonium salt and ammonia, the ammonium ion concentration being in at least a 3-fold excess over the magnesium ion concentration on a molar basis, to cause precipitation of magnesium omeprazole from the resultant mixed, organic solvent-free solution, and recovering the precipitated magnesium omeprazole therefrom.

2. The process of claim 1 in which an aqueous essentially organic solvent-free solution of the magnesium salt and the fully ionized ammonium salt, in which the ammonium ion concentration is in molar excess over the magnesium ion concentration, is mixed with an essentially organic solvent-free solution of omeprazole in concentrated ammonia.

3. The process of claim 2 wherein the ammonium ion concentration in said solution of magnesium salt and fully ionized ammonium salt is in molar excess of at least 5-fold over the magnesium ion concentration.

4. The process of claim 2 wherein the stoichiometric ratio of omeprazole to magnesium salts in the resultant mixed solution is from about 1.95 to 2.05.

5. The process of claim 4 wherein the magnesium salt is selected from the group consisting of magnesium chloride, magnesium bromide, magnesium iodide, magnesium sulphate and magnesium perchlorate.

6. The process of claim 5 wherein the fully ionized ammonium salt is selected from the group consisting of ammonium sulfate, ammonium chloride, ammonium nitrate, ammonium bromide and stoichiometric hydrates of the enumerated ammonium salts.

7. The process of claim 2 wherein the omeprazole-ammonium aqueous solution is added to the magnesium salt-ammonium salt aqueous solution.

8. The process of claim 1 wherein the magnesium salt is magnesium chloride or a stoichiometric hydrate thereof, or magnesium sulfate on a stoichiometric hydrate thereof.

* * * * *